(12) United States Patent
Gaber

(10) Patent No.: US 7,141,024 B2
(45) Date of Patent: Nov. 28, 2006

(54) MANEUVERABLE-COILED GUIDEWIRE

(76) Inventor: Benny Gaber, 29 Oren Street, Apt. 46, Haifa 34735 (IL)

( * ) Notice: Subject to any disclaimer, the term of this patent is extended or adjusted under 35 U.S.C. 154(b) by 405 days.

(21) Appl. No.: 10/699,387

(22) Filed: Nov. 4, 2003

(65) Prior Publication Data

US 2004/0092845 A1   May 13, 2004

(51) Int. Cl.
*A61B 5/00* (2006.01)
*A61M 25/00* (2006.01)

(52) U.S. Cl. ...................................... 600/585

(58) Field of Classification Search ................ 600/585, 600/434, 433, 435; 604/524, 528
See application file for complete search history.

(56) References Cited

U.S. PATENT DOCUMENTS 3,973,556 A * 8/1976 Fleischhacker et al. ..... 600/585
5,396,902 A * 3/1995 Brennen et al. ............ 600/585
5,480,382 A * 1/1996 Hammerslag et al. ...... 604/528
6,146,338 A * 11/2000 Gardeski et al. ............ 600/585
6,296,616 B1 * 10/2001 McMahon .................. 600/585
6,371,929 B1 * 4/2002 Steele ........................ 600/585
6,494,894 B1 * 12/2002 Mirarchi ..................... 606/190
6,497,681 B1 * 12/2002 Brenner ................. 604/164.05

* cited by examiner

*Primary Examiner*—Max F. Hindenburg
(74) *Attorney, Agent, or Firm*—Dekel Patent Ltd.; David Klein

(57) ABSTRACT

Guidewire apparatus including a guidewire including a coil, a distal portion of the coil being coated with a flexible coating, the coating being thicker on one side of a perimeter of the distal portion than on an opposite side of the perimeter of the distal portion, a pull wire disposed inside the guidewire connected at a proximal end thereof to a first stop member and at a distal end thereof to a second stop member, and an actuator disposed on the guidewire adapted to move the pull wire proximally such that proximally-directed pulling on the distal portion of the coil bends the distal portion towards the opposite side of the perimeter of the distal portion.

4 Claims, 3 Drawing Sheets

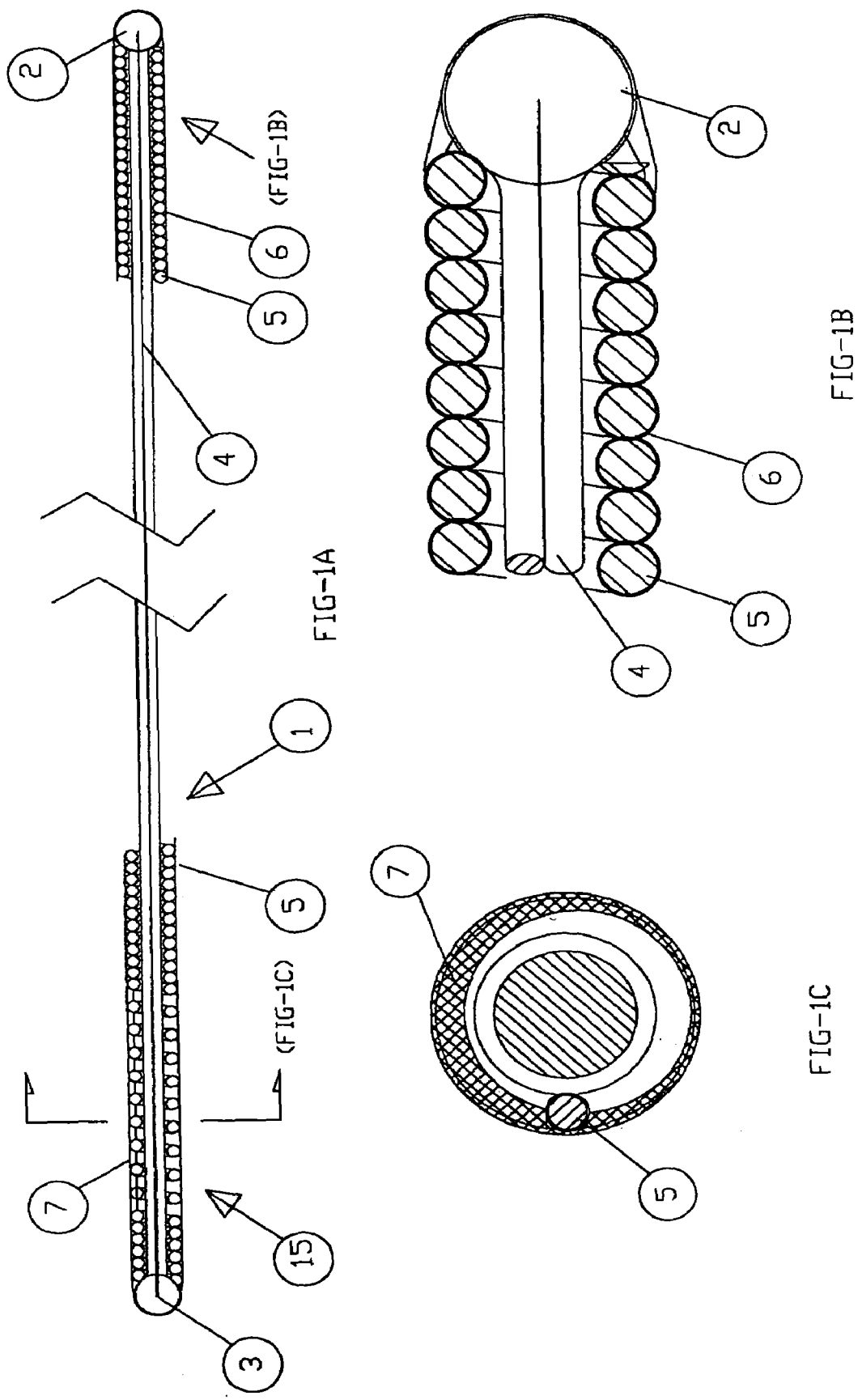

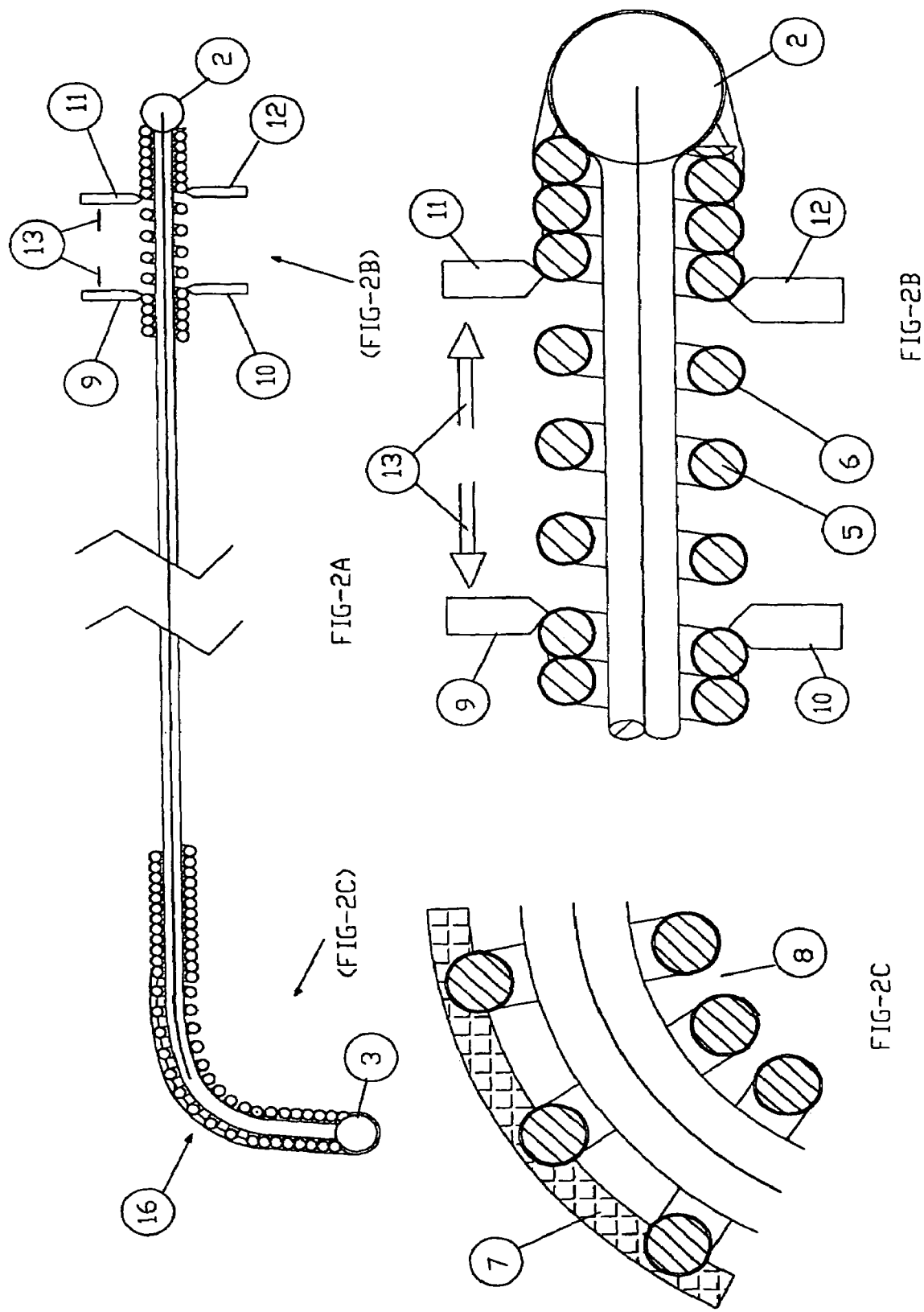

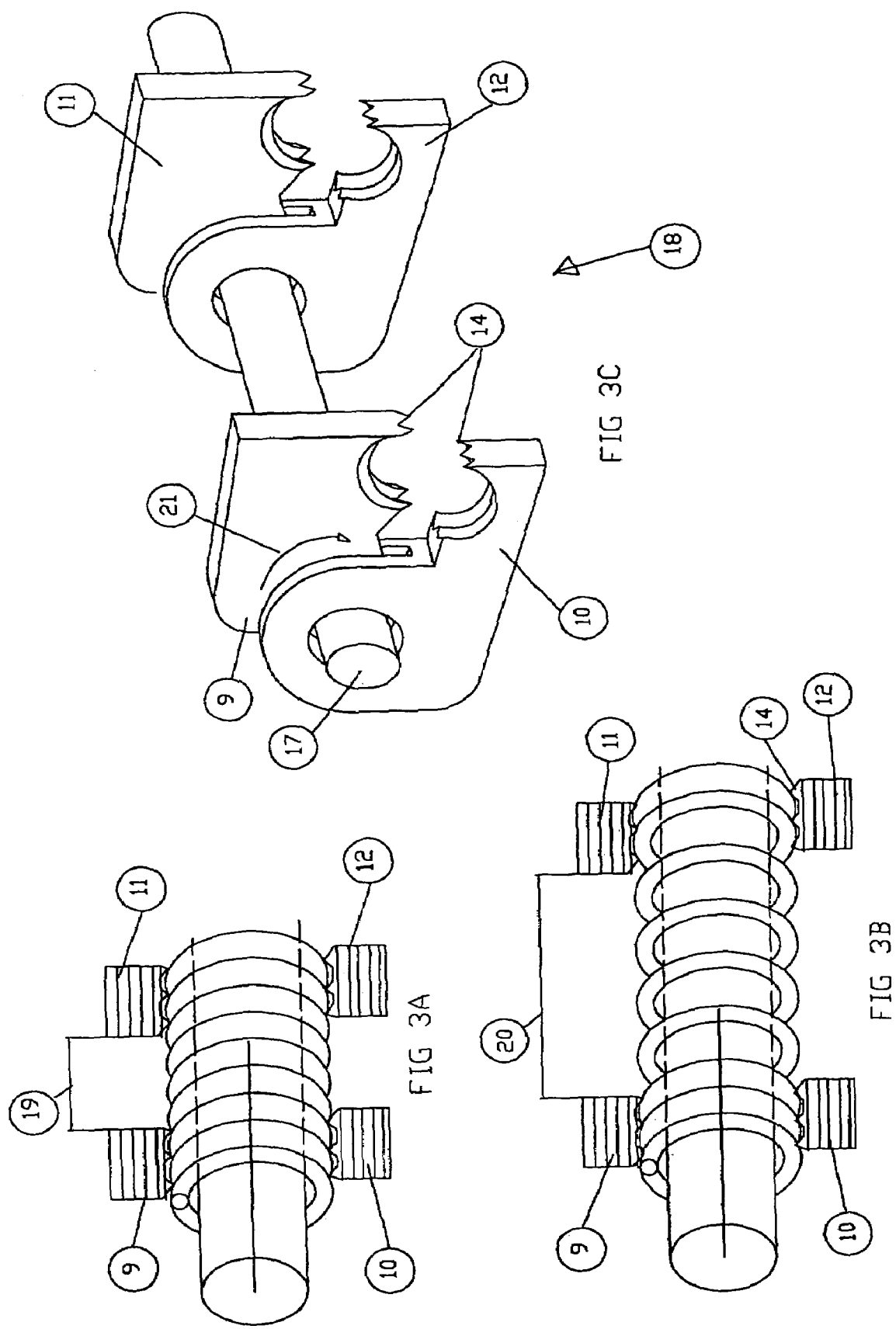

MANEUVERABLE-COILED GUIDEWIRE

FIELD OF THE INVENTION

The present invention relates generally to guiding apparatus in general, and particularly to deflectable guiding apparatus of a coiled guidewire used to guide catheters within the body lumens in procedures such as percutaneous transluminal coronary angioplasty (PTCA).

BACKGROUND OF THE INVENTION

In order to facilitate the advancement of catheters through a body lumen (e.g., an artery), a guidewire is often used to guide the catheter. In some of the cases, a coated coiled guidewire is used, with or without pre-bending the distal tip. At a bifurcation in the lumen it may be difficult to direct the tip into the desired branch. In order to bent and rotate the guidewire the surgeon, using both hands, may manipulate the proximal end (protruding from the body) with his fingers. Since the diameter of the guidewire is very small and the area is slippery with blood, directing the tip to a desired angle is a difficult and time-consuming task.

SUMMARY OF THE INVENTION

The present invention seeks to provide an easy maneuverability of a coated coiled guidewire around turns and bends in the body lumen and selectively deflect and rotate the distal tip using a handle on the proximal end.

In one embodiment, the guiding apparatus of the invention employs a coated coiled guidewire where the coils may be in contact with each other along the guidewire except for a small portion near the distal end in which they may be spaced from each other. An elastic material, such as PTFE, may coat the guidewire apparatus of the invention evenly along the guidewire apparatus of the invention except for the part where the coils may be spaced. In the spaced area the coating may be deeper on one side of the coil and may fill the gap between the coils towards the center of the guidewire apparatus of the invention.

A pull wire may be inserted into the coated, coiled guidewire apparatus of the invention and said pull wire may be connected to the guidewire at both ends. When the coils of the coated guidewire apparatus of the invention are pulled apart for some distance, in the proximal part, the pull wire attached to the distal end pulls the proximal end the same distance. The movement of the pull wire pulls the distal tip and applies compressive forces to the coils that close the gap, with the same distance, in the spaced area.

Since one side of the spaces between the coils, in the spaced area, may be filled with the coated material, the coils close the gap between themselves in the side where the coating does not fill the distance between the coils. The coiled guidewire then bends towards the side where the coating does not fill the distance between the coils.

A quick connection handle attachable to the coils in the distal end may enable movement of pulling apart the coils of the coated guidewire apparatus of the invention in the proximal part. The handle may also ease the rotation of the guidewire.

BRIEF DESCRIPTION OF THE DRAWINGS

The present invention will be understood and appreciated more fully from the following detailed description taken in conjunction with the appended drawings in which:

FIGS. 1A–1C are simplified illustrations of a maneuvered coated coiled guidewire constructed and operative in accordance with an embodiment of the present invention in its insertion status.

FIGS. 2A–2C are simplified illustrations of a maneuvered coated coiled guidewire constructed and operative in accordance with an embodiment of the present invention in its bent status.

FIGS. 3A–3C are simplified illustrations of an operative handle for the maneuvered coated coiled guidewire constructed and operative in accordance with an embodiment of the present invention.

DETAILED DESCRIPTION OF EMBODIMENTS

Reference is now made to FIGS. 1A–1C, which illustrate a maneuverable-coated coiled guidewire apparatus constructed and operative in accordance with an embodiment of the present invention.

The maneuvered-coated coiled guidewire apparatus may be constructed with a pull wire 4, disposed inside a coil 1, and connected at both ends thereof to a ball (first stop member) 2 at the proximal end and a ball (second stop member) 3 at the distal end. The coil 1 may be limited between ball 2 and ball 3. The coils 5 of coil 1 may be in touch with each other except for a part of the length of the coil, near the distal end marked by arrow 15, in which they may be spaced apart. A flexible coating 6, such as PTFE-Teflon, may coat the coil evenly except for the part 15 where the coils may be spaced apart, in which case the coating on one side of the coil may be deeper between the coils, as indicated by reference numeral 7. In other words, the coating 6 may be thicker on one side of the perimeter of the distal portion of coil 1 than on an opposite side of the perimeter of the distal portion. The coating 6 on the opposite side may have very little or even zero thickness, for example.

Reference is now made to FIGS. 2A–2C, which illustrate a maneuverable-coated coiled guidewire apparatus constructed and operative in accordance with an embodiment of the present invention in its bent position.

An actuator may be provided to bend the guidewire. In one embodiment, the actuator may comprise two matching jaws 9, 10 and 11, 12 that have a thread 14 that may engage the coil 1. Jaws 9 and 10 may be paired and oppose each other. Jaws 11 and 12 may be paired and oppose each other as well. Both pairs may be moved in opposite directions along arrow 13. Applying a pull movement to the pairs of jaws by the distance marked by arrows 13, after matching the thread of the two pairs of jaws upon the coil 1, causes the coils between the pairs to stretch and spread by the same distance. The spread movement on the coil pushes the ball 2 at the proximal end with regard to the pair of jaws 9 and 10. The pull wire 4, which may be attached to the ball 2, then pulls the distal end ball 3 in the direction of the proximal end. Since the coils 5 of coil 1 may be in contact with each other, only the spaced area 15 may be compressed. Since the spaced area 15 of the coil 1 may be filled, on one side, with the coating material 6 only the other side of the coil allows the coils 5 to come closer to each other 8, thus causing the spaced area to create a curve in the coil 1 distal end marked by arrow 16. The more movement along arrow 13 the tighter will be the curve 16 created in the spaced area.

Reference is now made to FIGS. 3A–3C, which illustrate a connection between the handle jaws 9, 10, 11, 12 and the maneuverable-coated coiled guidewire apparatus constructed and operative in accordance with a preferred embodiment of the present invention.

A handle 18 contains two matching jaws: 9; 10 and 11; 12 able to engage the coil 1 with threads 14. Jaws 9 and 10 may be paired and oppose each other about the axis 17 in the direction marked by arrow 18 and also jaws 11 and 12 may be paired and oppose each other about the axis 17 in the direction marked by arrow 21. Both pairs may be moved in opposite directions along axis 17 in the direction marked by arrow 13.

FIG. 3A shows the connection between the handle jaws thread 14 and the coil 1 in the proximal end of coil 1 (protruding outside the patient's body) where the distance between the two pairs 9 10 and 11 12 is in its close position marked by arrow 19.

FIG. 3B shows the connection between the handle jaws thread 14 and the coil 1 in the proximal end of coil 1 where the distance between the two pairs 9;10 and 11;12 is in its opened position marked by arrow 20.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. Guidewire apparatus comprising:

a guidewire comprising a core-less coil, a distal portion of said coil being coated with a flexible coating, said coating being thicker on one side of a perimeter of said distal portion than on an opposite side of the perimeter of said distal portion, said coating extending between adjacent windings of said coil on the thicker side of the perimeter;

a pull wire disposed inside said guidewire connected at a proximal end thereof to a first stop member and at a distal end thereof to a second stop member; and an actuator disposed on said guidewire adapted to move said pull wire proximally such that proximally-directed pulling on the distal portion of said coil bends said distal portion towards said opposite side of the perimeter of said distal portion.

2. The guidewire apparatus according to claim 1, wherein said actuator comprises jaws that engage said coil.

3. The guidewire apparatus according to claim 2, wherein separating said jaws from each other stretches said coil and pushes said first stop member in the proximal direction.

4. The guidewire apparatus according to claim 1, wherein said coating on the opposite side of the perimeter of said distal portion has zero thickness.

* * * * *